United States Patent
Sharkey et al.

(10) Patent No.: US 10,729,550 B2
(45) Date of Patent: Aug. 4, 2020

(54) DUAL MOBILITY ACETABULAR CUP ASSEMBLY FOR ARTIFICIAL HIP JOINT

(71) Applicant: Corentec Co., LTD., Cheonan-si, Chungcheongnam-do (KR)

(72) Inventors: Peter F. Sharkey, Villanova, PA (US); Javad Parvizi, Gladwyne, PA (US)

(73) Assignee: Corentec Co., Ltd, Cheonan-si, Chungcheongnam-do (KR)

( * ) Notice: Subject to any disclaimer, the term of this patent is extended or adjusted under 35 U.S.C. 154(b) by 152 days.

(21) Appl. No.: 15/659,988

(22) Filed: Jul. 26, 2017

(65) Prior Publication Data
US 2018/0028322 A1 Feb. 1, 2018

Related U.S. Application Data

(60) Provisional application No. 62/367,908, filed on Jul. 28, 2016.

(51) Int. Cl.
| | |
|---|---|
| *A61F 2/34* | (2006.01) |
| *A61F 2/30* | (2006.01) |
| *A61F 2/46* | (2006.01) |
| *A61B 17/16* | (2006.01) |
| *A61B 90/00* | (2016.01) |
| *A61B 17/14* | (2006.01) |
| *A61B 17/02* | (2006.01) |
| *A61B 17/15* | (2006.01) |
| *A61B 17/92* | (2006.01) |

(Continued)

(52) U.S. Cl.
CPC .............. *A61F 2/34* (2013.01); *A61B 17/025* (2013.01); *A61B 17/0218* (2013.01); *A61B 17/149* (2016.11); *A61B 17/15* (2013.01); *A61B 17/1613* (2013.01); *A61B 17/1631* (2013.01); *A61B 17/1659* (2013.01); *A61B 17/1664* (2013.01); *A61B 17/1668* (2013.01); *A61B 17/92* (2013.01); *A61B 90/06* (2016.02); *A61F 2/30724* (2013.01); *A61F 2/4637* (2013.01); *A61B 17/1633* (2013.01); *A61B 17/1742* (2013.01); *A61B 2017/00876* (2013.01); *A61B 2017/00991* (2013.01); *A61B 2017/0275* (2013.01); *A61B 2017/922* (2013.01); *A61B 2090/064* (2016.02); *A61F 2002/30565* (2013.01); *A61F 2002/30617* (2013.01); *A61F 2002/30718* (2013.01); *A61F 2002/30719* (2013.01); *A61F 2002/3208* (2013.01); *A61F 2002/348* (2013.01); *A61F 2002/4666* (2013.01)

(58) Field of Classification Search
USPC .......................................... 623/22.21–22.39
See application file for complete search history.

(56) References Cited

U.S. PATENT DOCUMENTS

| | | | | |
|---|---|---|---|---|
| 5,609,648 | A * | 3/1997 | Oehy .................. | A61F 2/30744 623/22.19 |
| 8,123,814 | B2 * | 2/2012 | Meridew ............. | A61F 2/30734 623/22.19 |

(Continued)

*Primary Examiner* — Yashita Sharma
(74) *Attorney, Agent, or Firm* — Workman Nydegger

(57) ABSTRACT

An implant for an artificial hip joint and, more specifically, a dual mobility acetabular cup assembly for an artificial hip joint is configured to have improved locking mechanism between a liner and a shell and improved resistance to micromotion and to guide the liner into the shell with proper orientation by providing stable liner-shell fastening structure to the acetabular cup assembly.

16 Claims, 12 Drawing Sheets

(51) Int. Cl.
*A61F 2/32* (2006.01)
*A61B 17/00* (2006.01)
*A61B 17/17* (2006.01)

(56) References Cited

U.S. PATENT DOCUMENTS

| 8,771,366 B2* | 7/2014 | Whitaker | A61F 2/32 |
| | | | 623/22.11 |
| 2008/0255672 A1* | 10/2008 | Gil | A61F 2/34 |
| | | | 623/22.28 |
| 2010/0131073 A1* | 5/2010 | Meridew | A61F 2/34 |
| | | | 623/22.28 |
| 2013/0204388 A1* | 8/2013 | Meridew | A61F 2/34 |
| | | | 623/22.36 |

* cited by examiner

DUAL MOBILITY ACETABULAR CUP ASSEMBLY FOR ARTIFICIAL HIP JOINT

CROSS-REFERENCE TO RELATED APPLICATIONS

This application claims the benefit of U.S. Provisional Application No. 62/367,908, filed Jul. 28, 2016, which is incorporated herein by specific reference.

TECHNICAL FIELD

The present invention relates to an implant for an artificial hip joint and, more specifically, to a dual mobility acetabular cup assembly for an artificial hip joint. According to the present invention, provided is a dual mobility acetabular cup assembly for an artificial hip joint, configured to have improved locking mechanism between a liner and a shell and improved resistance to micromotion and to guide the liner into the shell with proper orientation by providing stable liner-shell fastening structure to the acetabular cup assembly.

BACKGROUND

Of many joints in a human body, formed is a hip joint region being a cartilage portion in friction contact with a femur being a bone of lower limb below a hip, referred to as an acetabulum, in a pelvis, which is a hipbone. The acetabulum enables the pelvis and the femur to rotate relatively to each other in a certain range of angles. In some cases, the hip joint region in the human body cannot be restored due to wear of a joint area, aging of bone tissue, and accidents. This unrestorability is caused by natural loss due to upright walking, heredity cause, excessive workouts and safety accidents. In this case, pain is accompanied at regions of bones touching with each other between interconnected bones and the hip joint is damaged. An artificial hip joint device is used to replace the damaged joint for facilitating relative rotation and flexing as in its native state. In general, an artificial hip joint system includes an acetabular cup coupled to an acetabulum by insertion and a head of a femoral stem inserted inside a femur, and the head can rotate within a certain range inside the acetabular cup.

Likewise, a dual mobility acetabular cup assembly of several acetabular cup assemblies used in total hip arthroplasty (THA) utilizing an artificial hip joint device was developed in 1970's, and has been used and continuously improved up until now to provide as large range of motion as possible in a stable environment and reduced wear capability.

Basically, as shown in FIGS. 1 and 2, a dual mobility acetabular cup 400 comprises: an acetabular cup 410, a liner 420, an insert 430, and a ball head 440. The insert 430 being rotatable is coupled inside the acetabular cup 410 through the liner 420, and the ball head 440 being rotatable is coupled inside the insert 430, thereby making dual bearing. The liner 420 is fixed in an inner face of the acetabular cup 410, i.e., between the acetabular cup 410 and the insert 430.

The dual mobility acetabular cup 400 provides two articulating elements by having two bearing surfaces. Of the two bearings, one being an external bearing is disposed between the acetabular cup 410 and the insert 430 and the other being an internal bearing is disposed between the insert 430 and the ball head 440. A majority of movement occurs in the internal bearing and the external bearing moves when a normal movement range is exceeded.

In total hip arthroplasty, dislocation of an implant may occur after surgery. Such dislocation after THA conservatively happens 2 to 4 percent. The patient becomes unable to move his or her body and suffers from severe pain and the doctor is placed under pressure of performing emergency operation when dislocation occurs at work hours or night. Also, this condition diminishes life quality of the patient and may cause a medical dispute.

Innovations in the THA implant have been focused mostly on reducing an incidence of prosthetic instability over the past 20 years. As a result, larger heads, lipped liners, modularity, metal on metal THA, metal on metal resurfacing, dual mobility THA, constrained liners, smaller trunnions/neck and the like have appeared. Of these, it is known that the dual mobility acetabular cup described above reduces a possibility of occurrence of dislocation by increasing range of motion (ROM).

However, such dual mobility acetabular cup has some issues to be improved.

In the first place, intra-prosthetic dislocation inside the artificial implant requires open reduction, which is as problematic as dislocation of a head from a mobile polyethylene (PE) liner. However, this problem can be solved by using cross-linked PE of high quality.

In prior art, the liner 420 coupled inside the acetabular cup 410 protrudes toward a rim 422 and collides with a stem neck as shown in FIG. 3, which may cause micromotion and fretting corrosion. This is because the coupling of the two components is accomplished by taper locking of the rim 422.

Therefore, there is a need for developing a non-modular dual mobility acetabular cup which can improve fastening mechanism between a liner and a shell and prevent fretting corrosion.

SUMMARY OF THE INVENTION

Technical Problem

The present invention has been made in an effort to solve the problems.

An object of the present invention is to provide a dual mobility acetabular cup assembly for an artificial hip joint comprising a liner-shell fastening structure having no parts protruding outward to provide stable connection and to prevent interference with a femoral neck.

Another object of the present invention is to provide a dual mobility acetabular cup assembly for an artificial hip joint comprising a liner-shell fastening structure having no parts protruding outward, thereby preventing fretting corrosion.

Yet another object of the present invention is to provide a dual mobility acetabular cup assembly for an artificial hip joint with improved resistance to micromotion by including a liner-shell fastening structure having no parts protruding outward.

Yet another object of the present invention is to provide a dual mobility acetabular cup assembly for an artificial hip joint, capable of mounting and orienting the liner in an exact position inside the shell.

Yet another object of the present invention is to provide a dual mobility acetabular cup assembly for an artificial hip joint, capable of decreasing wear.

Technical Solutions

The present invention has been made in an effort to solve the problems.

According to one embodiment of the present invention, a dual mobility acetabular cup assembly for an artificial hip joint comprises: a shell having one or more penetration holes; and a liner disposed at an inner side of the shell and having a protrusion insertable in the penetration hole.

According to another embodiment of the dual mobility acetabular cup assembly, the protrusion is configured to fix the liner in the shell by being inserted in the penetration hole.

According to still another embodiment of the dual mobility acetabular cup assembly, the penetration hole is tapered outwardly from an inner face of the shell.

According to still another embodiment of the dual mobility acetabular cup assembly, the protrusion has a shape corresponding to the tapered penetration hole for fit connection to the penetration hole.

According to sill another embodiment of the present invention, the dual mobility acetabular cup assembly further comprises a plug insertable in the penetration hole.

According to still another embodiment of the dual mobility acetabular cup assembly, a through-hole configured to receive the protrusion and penetrate the plug in a longitudinal direction is formed in the plug.

According to still another embodiment of the dual mobility acetabular cup assembly, the protrusion and the through-hole are engaged by taper connection.

According to still another embodiment of the dual mobility acetabular cup assembly, external threads are formed in an outer circumferential face of the plug such that the plug is received in the penetration hole, and internal threads capable of being fastened with the external threads are formed in the penetration hole.

According to still another embodiment of the dual mobility acetabular cup assembly, the protrusion is tapered in an outward direction from a surface of the liner and the plug includes a tapered through-hole which penetrates the plug in the longitudinal direction such that the plug receives the protrusion.

According to still another embodiment of the dual mobility acetabular cup assembly, wherein the shell is made from titanium.

According to still another embodiment of the dual mobility acetabular cup assembly, wherein the liner is made from one of cobalt-chrome or ceramic.

Advantageous Effect

According to embodiments of the present invention, the present invention can obtain the following effects.

According to the present invention, provided is a dual mobility acetabular cup assembly for an artificial hip joint comprising a liner-shell fastening structure having no parts protruding outward to provide stable connection and to prevent interference with a femoral neck.

According to the present invention, provided is a dual mobility acetabular cup assembly for an artificial hip joint comprising a liner-shell fastening structure having no parts protruding outward, capable of preventing fretting corrosion.

According to the present invention, provided is a dual mobility acetabular cup assembly for an artificial hip joint with improved resistance to micromotion by including a liner-shell fastening structure having no parts protruding outward.

According to the present invention, provided is a dual mobility acetabular cup assembly for an artificial hip joint, capable of mounting and orienting the liner in an exact position inside the shell.

According to the present invention, provided is a dual mobility acetabular cup assembly for an artificial hip joint, capable of decreasing wear.

The effects of the present invention are not limited to the above-mentioned effects. Other effects not stated above will be clearly understood by a person having ordinary skill in the art based on the following disclosures.

BEST DESCRIPTION OF THE DRAWINGS

DETAILED DESCRIPTION

Figure 1:
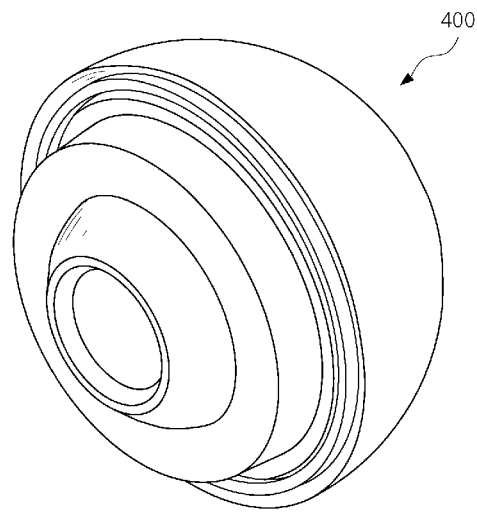
FIG. 1 illustrates a perspective view of an existing dual mobility acetabular cup assembly.
Figure 2:
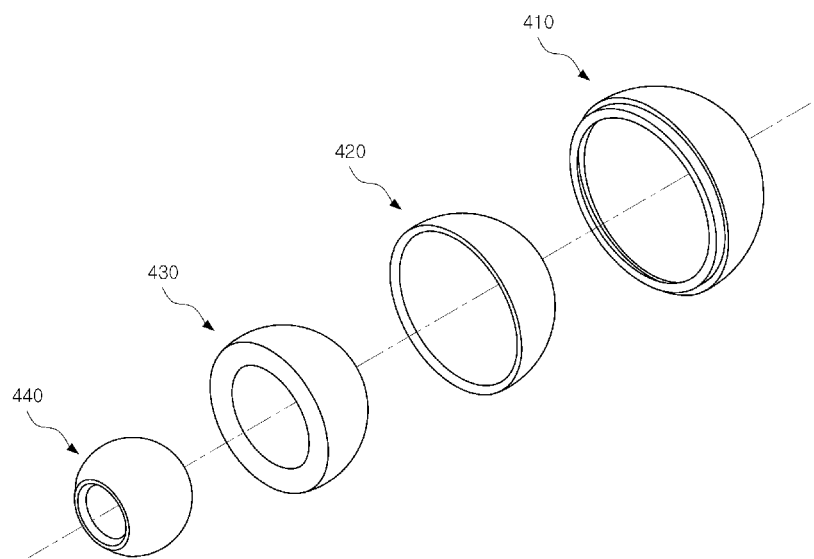
FIG. 2 illustrates an exploded view of the dual mobility acetabular cup assembly shown in FIG. 1.
Figure 3:
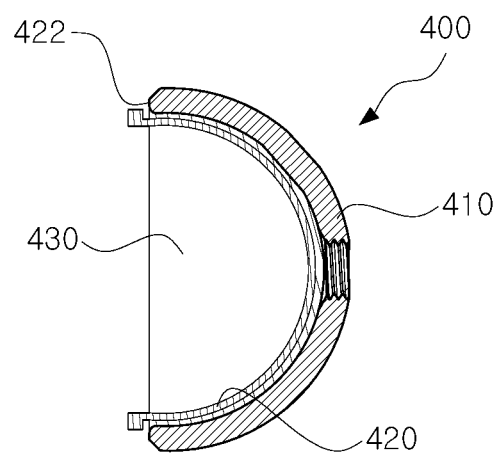
FIG. 3 illustrates another example of an existing dual mobility acetabular cup assembly.

Hereinafter, a dual mobility acetabular cup assembly for an artificial hip joint according to the present invention is described in detail. Well-known functions or constructions will not be described in detail in case they may unnecessarily obscure the understanding of the present invention.

Specific structural and functional descriptions of embodiments of the present invention disclosed herein are only for illustrative purposes of the embodiments of the present invention. The embodiments according to the spirit and scope of the present invention can be variously modified in many different forms. While the present invention will be described in conjunction with exemplary embodiments thereof, it is to be understood that the present description is not intended to limit the present invention to those exemplary embodiments. On the contrary, the present invention is intended to cover not only the exemplary embodiments, but also various alternatives, modifications, equivalents and other embodiments that may be included within the spirit and scope of the present invention as defined by the appended claims.

The same reference numerals represent the same elements throughout the specification. It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

Below exemplary embodiments of the present invention are described in detail with reference to accompanying drawings. The invention may, however, be embodied in many different forms and should not be construed as being limited to the embodiments set forth herein; rather, these embodiments are provided so that this disclosure will be thorough and complete, and will fully convey the concept of the invention to those skilled in the art.

According to the present invention, a dual mobility acetabular cup assembly comprises: a shell; and a liner disposed at inner side of the shell.

Figure 4:
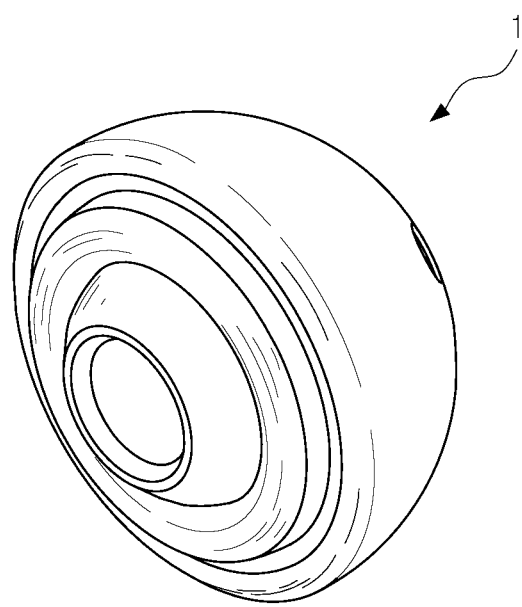
FIG. 4 illustrates a perspective view of a dual mobility acetabular cup assembly according to one embodiment of the present invention.
Figure 5:
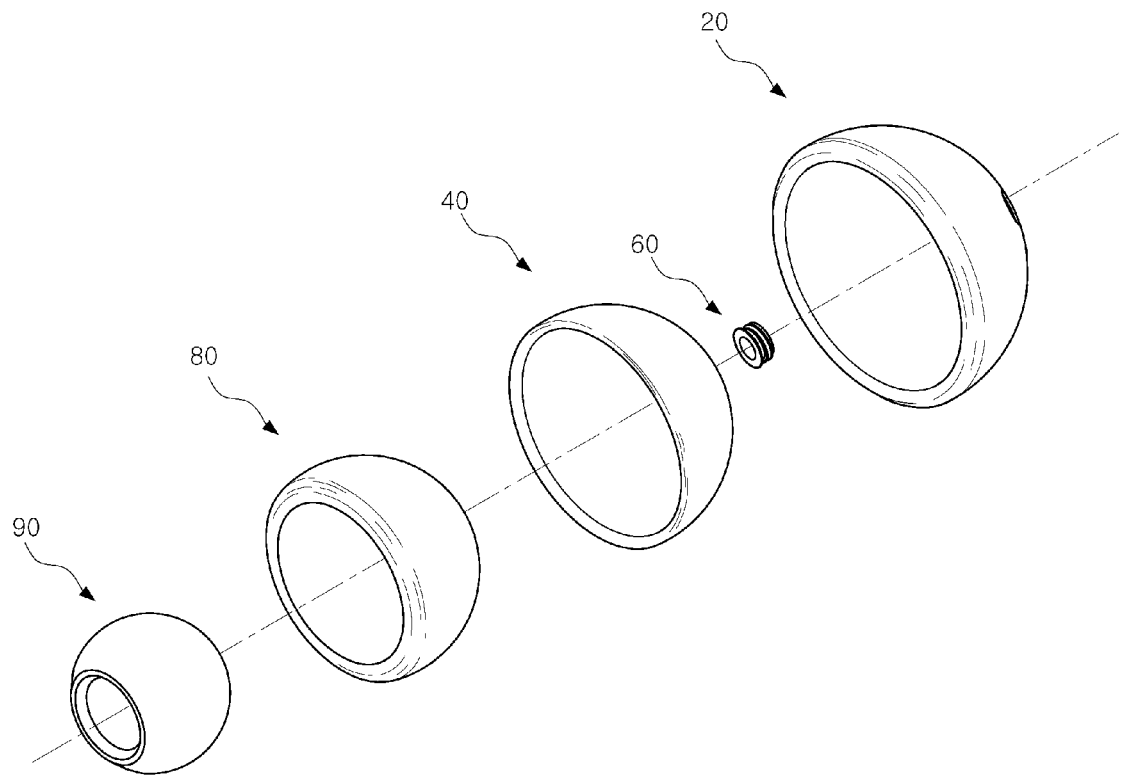
FIG. 5 illustrates an exploded view of the dual mobility acetabular cup assembly shown in FIG. 4.

FIG. 4 shows a perspective view of a dual mobility acetabular cup assembly for an artificial hip joint according to one embodiment of the present invention, and FIG. 5 shows an exploded view of the dual mobility acetabular cup assembly in FIG. 4. Referring to FIGS. 4 and 5, the dual mobility acetabular cup assembly for an artificial hip joint according to one embodiment of the present invention is now described.

Figure 6A:
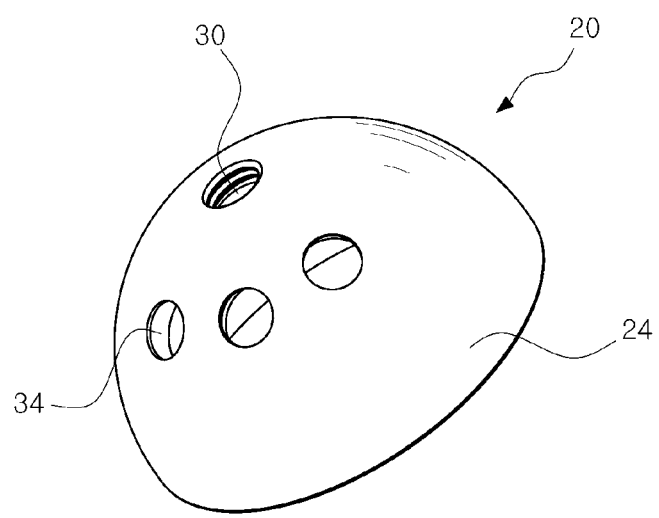
FIGS. 6a to 6c show a shell according to one embodiment of the present invention.
Figure 6B:
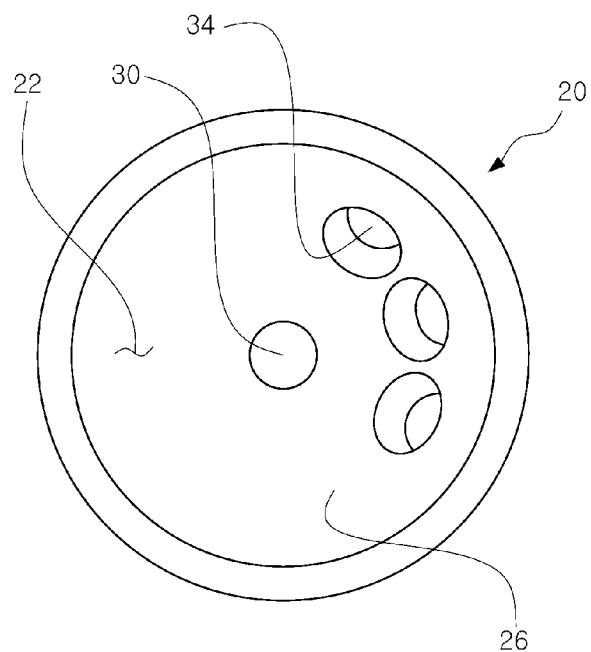
Figure 6C:
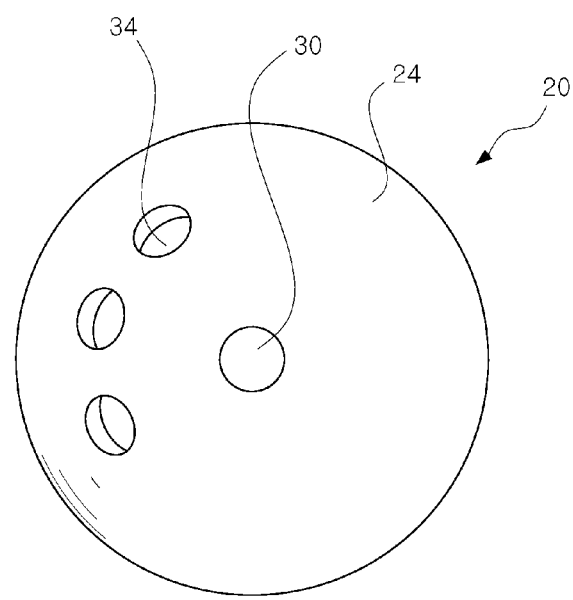

Referring to FIGS. 6a to 6c, a dual mobility acetabular cup assembly 1 for an artificial hip joint according to the present invention comprises a shell 20. FIG. 6a shows a perspective view of a shell, FIG. 6b shows a bottom view of the shell, and FIG. 6c shows a top view of the shell.

The shell 20, being dome-shaped or a hemisphere with an empty space inside, has a space 22 inside. The shell 20 is placed outermost from a femoral stem when the acetabular cup assembly 1 is mounted on the femoral stem (not shown).

The shell 20 comprises an outer face 24 and an inner face 26 opposite to the outer face 24. Specifically, the shell 20 includes the inner face 26 spaced from the outer face 24 by certain thickness and forming an opposing side of the outer face 24.

One or more penetration holes 30 are formed in the shell 20. The penetration hole 30 is a hole which penetrates the outer face 24 and the inner face 26 of the shell 20 and is formed approximately in a center part, preferably. Also, the penetration hole 30 may be used as a hole in which an impactor (not shown) used to insert the shell 20 to a human body is inserted.

A plurality of holes 34 may be formed around the penetration hole 30. The plurality of holes 34 penetrate from the outer face 24 to the inner face 26 of the shell 20 as the penetration hole 30. Preferably, the plurality of holes 34 are formed at a certain radial distance apart from the penetration hole 30 and three or more holes may be formed. The holes 34 are used for screw connection.

The shell 20 may be made from any material known in the art and widely used in a hip joint implant, but, preferably made from titanium. For example, the shell 20 may be formed by cobalt-chrome or the like, but preferably by titanium. In case the shell 20 is made from titanium, bone ingrowth can be improved compared to the case where the shell is made from cobalt-chrome.

Figure 7A:
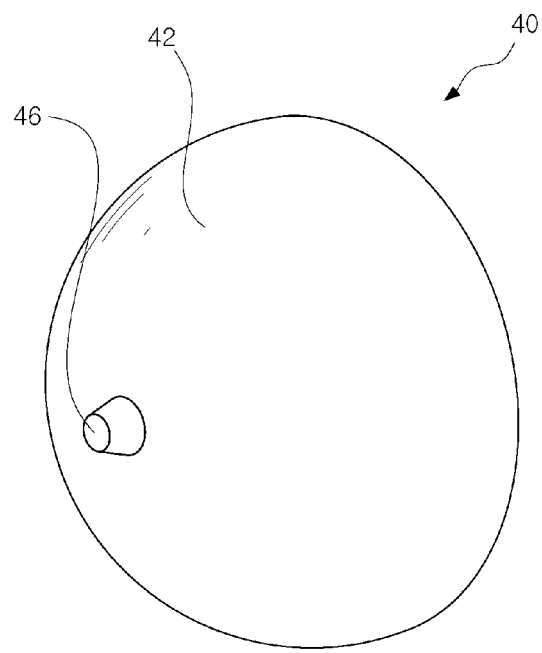
FIGS. 7a to 7c show a liner according to one embodiment of the present invention.
Figure 7B:
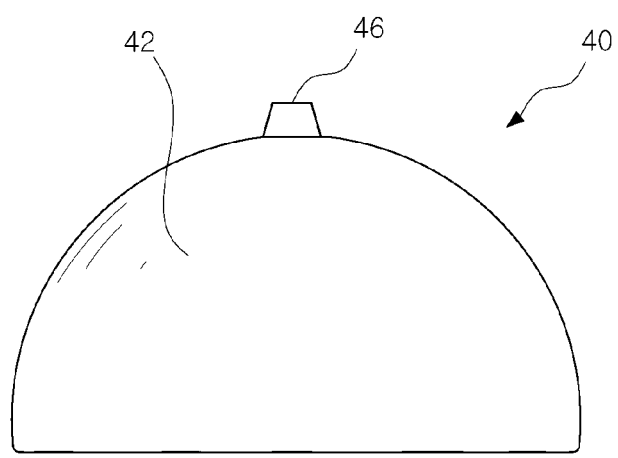
Figure 7C:
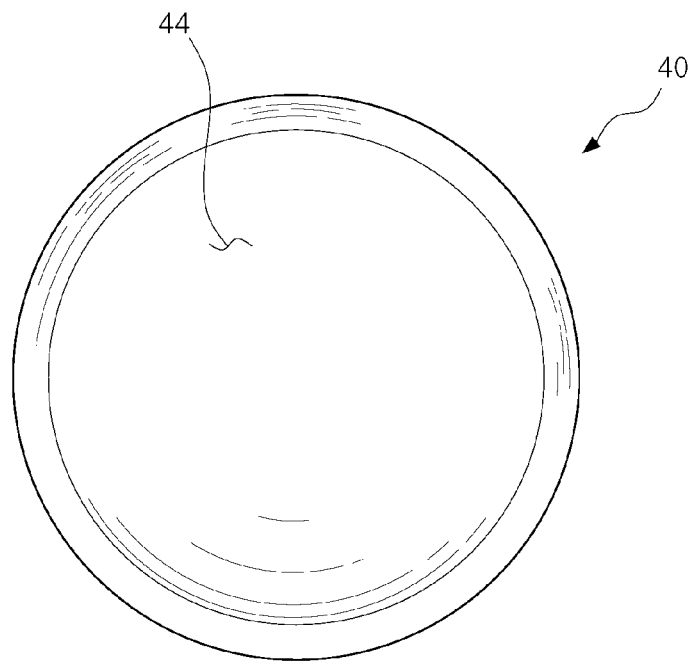

In addition, referring to FIGS. 7a to 7c, the dual mobility acetabular cup assembly for an artificial hip joint comprises a liner 40. FIG. 7a shows a perspective view of a liner; FIG. 7b shows a side view of the liner; and FIG. 7c shows a top view of the liner.

The liner 40 is disposed at the inner face 26 of the shell 20 and the liner 40 has an outer-side face 42 which has a shape corresponding to the shape of the inner face 26 of the shell 20. The liner 40 has the outer-side face 42 facing the shell 20 and an inner-side face 44 opposite to the outer-side face 42. The liner 40 is formed by extending from the inner-side face 44 to the outer-side face 42 or from the outer-side face 42 to the inner-side face 44 by certain thickness.

The liner 40 includes a protrusion 46 protruding outward from the outer-side face 42. The protrusion 46 may be formed approximately in a center part of the liner 40. In case the protrusion 46 and the penetration hole 30 are formed approximately in the center part of the liner 40 and the shell 20, respectively, the liner 40 and the shell 20 are positioned such that center parts of the liner 40 and the shell 20 are substantially aligned.

As described above, the liner 40 has a solid face. That is, the liner 40 has no holes to prevent wear of an insert disposed at an inner side of the liner 40 by holes formed in the shell 20.

Such liner 40 may be made from any material known in the art and used for the liner 40 of an implant but preferably made from cobalt-chromium alloy. According to another aspect of the present invention, the liner 40 may be formed from ceramic instead of cobalt-chromium alloy. The liner 40 made from ceramic can decrease wear compared to the liner 40 made from cobalt-chromium alloy.

The protrusion 46 is formed to be inserted in the penetration hole 30 formed in the shell 20. It is preferable to form the shapes of the protrusion 46 and the penetration hole 30 to be identical for easy insertion. According to one aspect of the present invention, the protrusion 46 can be fit into the penetration hole 30. For instance, an interference fit, a press fit or the like may be employed.

Such fit may be realized through Morse taper connection. More specifically, the penetration hole 30 may be formed as being tapered so that diameter of the hole decreases from the inner face 26 to the outer face 24 of the shell 20. Correspondingly, the protrusion 46 of the liner 40, inserted in the penetration hole 30, may be formed as being tapered so that the diameter of the protrusion 46 decreases outward from the outer-side face 42. In this case, an outer circumference of the protrusion 46 and an inner circumference of the penetration hole are about the same, and the protrusion 46 is fixed in the penetration hole 30 by fit connection and, further, the liner 40 is fixed in the shell 20.

Figure 8A:
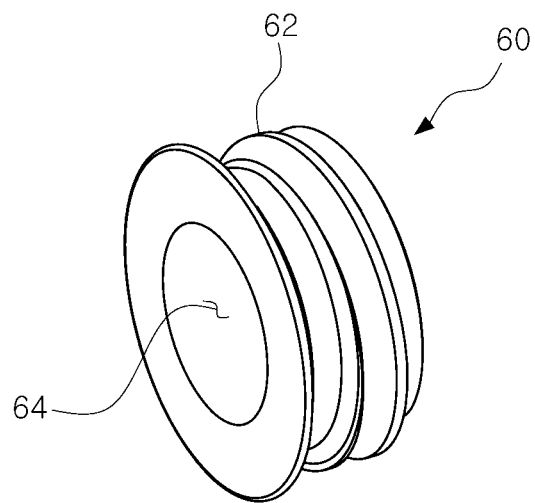
FIGS. 8a to 8f show a plug according to one embodiment of the present invention.
Figure 8B:
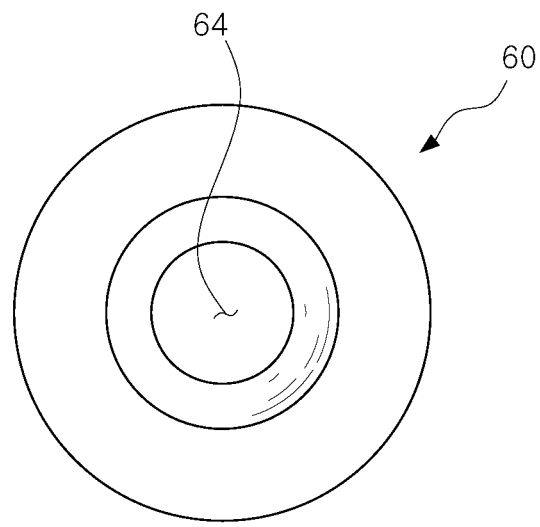
Figure 8C:
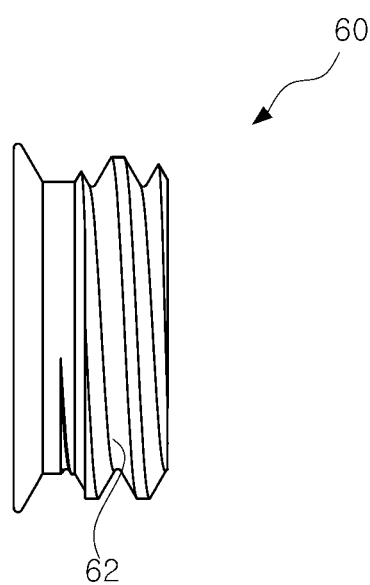
Figure 8D:
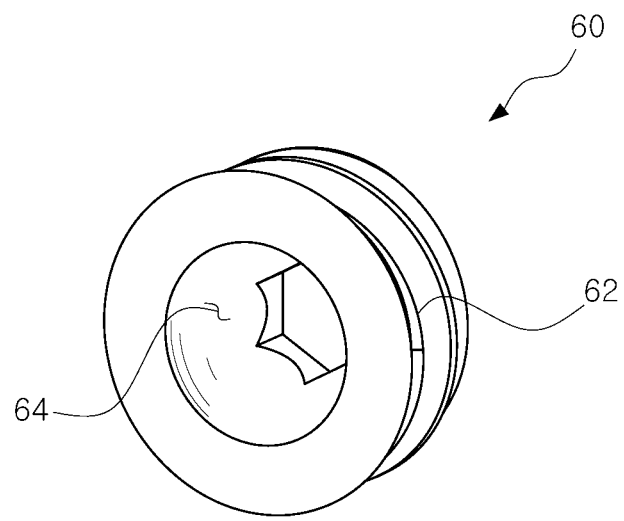
Figure 8E:
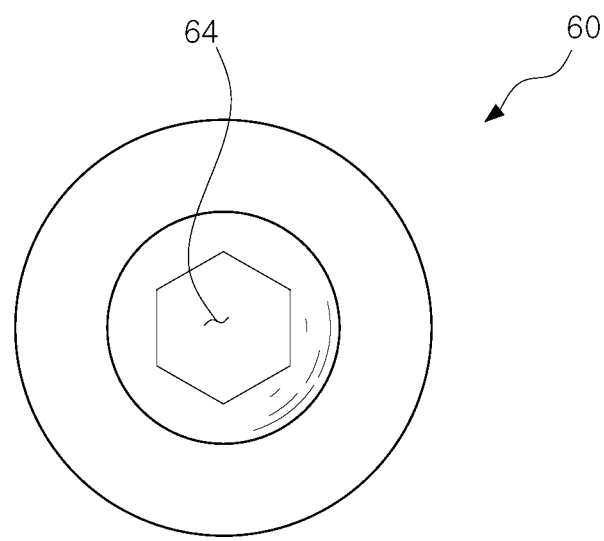
Figure 8F:
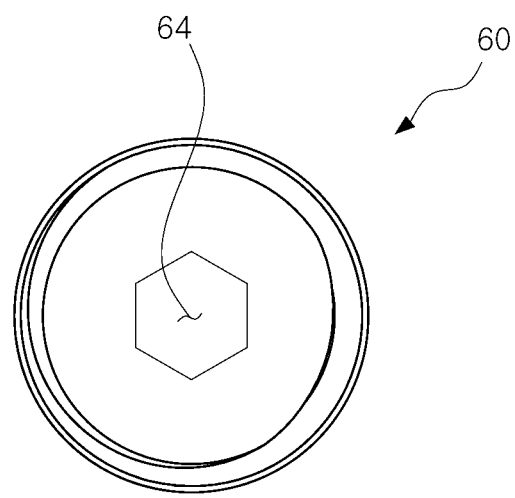
Figure 9:
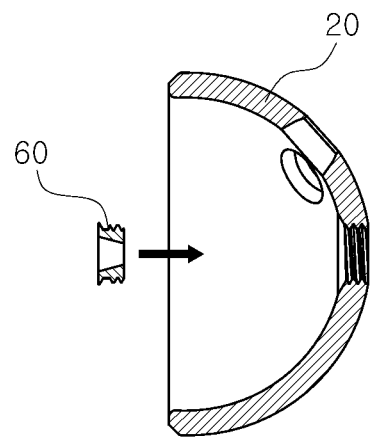
FIG. 9 illustrates a plug coupled to a penetration hole according to embodiments of the present invention.

According to another embodiment of the present invention, the dual mobility acetabular cup assembly for an artificial hip joint includes a plug 60. FIG. 8a shows a perspective view of a plug according to one aspect of the present invention, FIG. 8b shows a top view of the plug, FIG. 8c shows a side view of the plug, FIG. 8d shows a perspective view of the plug according to another aspect of the present invention, FIG. 8e shows a bottom view of the plug shown in FIG. 8d, and FIG. 8f shows a top view of the plug shown in FIG. 8d.

The plug 60 is formed to be inserted in the penetration hole 30 of the shell 20. As will be described below, the plug 60 enables stable connection between the shell 20 and the liner 40. The plug 60 may be mounted in the penetration hole 30 by fit connection. In addition, referring to FIG. 10, the plug 60 may be mounted in the penetration hole 30 by screw connection. To be illustrated, external threads 62 may be formed in an outer circumferential face of the plug 60 to be received inside the penetration hole 30, and internal threads corresponding to the external threads may be formed in the penetration hole 30 to be fastened with the external threads 62. The plug 60 having the external threads 62 are mounted in the penetration hole 30 by screw connection.

Figure 10:
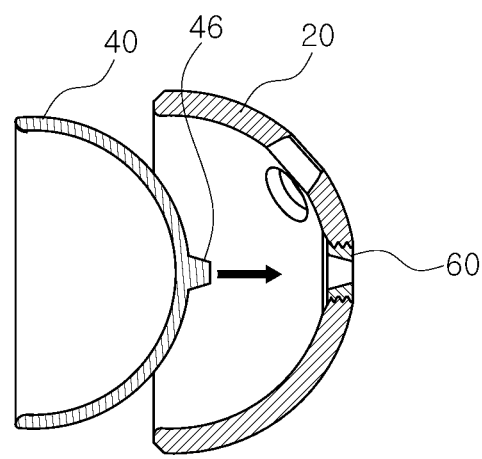
FIG. 10 illustrates a protrusion of a liner coupled to a shell mounted with a plug.

Referring to FIG. 10, a through-hole 64 penetrating in a longitudinal direction of the plug 60 may be formed in the plug for stably connecting the shell 20 with the liner 40. The protrusion 46 of the liner 40 is configured to be received in the shell 20 through the through-hole 64. In this instance, the through-hole 64 may be formed identically to the shape of the protrusion 46 for connection, such as fit connection.

For examples, the protrusion 46 and the through-hole 64 may be connected by tapered interference fit. The protrusion 46, as described above, is tapered such that the circumference decreases outward from the outer-side face 42, while the through-hole 64 is tapered from an inner side to the outer side of the shell 20. In other words, the through-hole 64 and the protrusion 4 may be formed to be connected by Morse taper. Through such connection, the liner 40 is better stably coupled to the shell 20, and in correct orientation. Moreover, rotation and separation of the liner 40 are prevented, and the liner 40 and the shell 20 are stably fastened with each other.

As shown in FIGS. 8a to 8c, the cross section of the through-hole 64 may be circular, or the cross section of the through-hole 64 may be polygonal, e.g. hexagonal, as shown in FIGS. 8d to 8f. As illustrated above, in case the tapered through-hole 64 having a circular cross section is used, the protrusion 46 is configured to have a tapered shape with a circular cross section. In another case where the tapered through-hole 64 has a polygonal cross section, the protrusion 46 is configured to have a tapered shape with a corresponding polygonal cross section.

The acetabular cup assembly for an artificial hip joint according to the present invention provides a liner-shell fastening structure which has no outwardly protruding parts to solve the problems above, thereby preventing micromotion of the liner by stable connection. In addition, the protrusion 46 guides the liner 40 to be seated in an exact mounting position inside the shell.

That is, a rim part of the liner protrudes outwardly for connecting the liner to the shell in the prior acetabular cup assemblies, which interferes with the femoral stem and causes fretting corrosion. On the other hand, according to the present invention, the acetabular cup assembly utilizes locking mechanism between the penetration hole 30 and the protrusion 46 and removes the rim part protruding outwardly, thereby stably coupling the shell 20 to the liner 40.

Figure 11A:
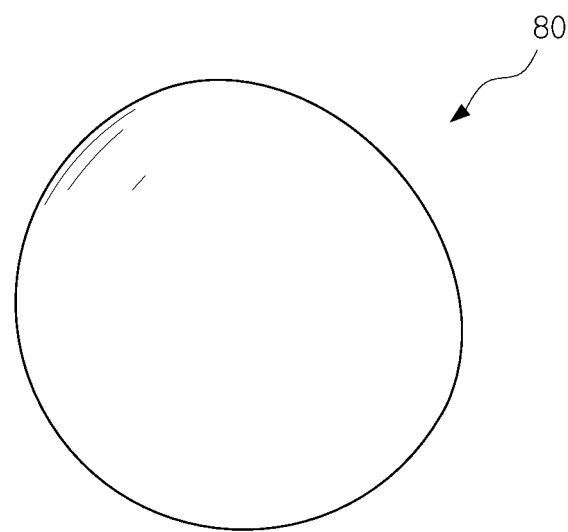
FIGS. 11a and 11b show an insert according to one embodiment of the present invention.
Figure 11B:
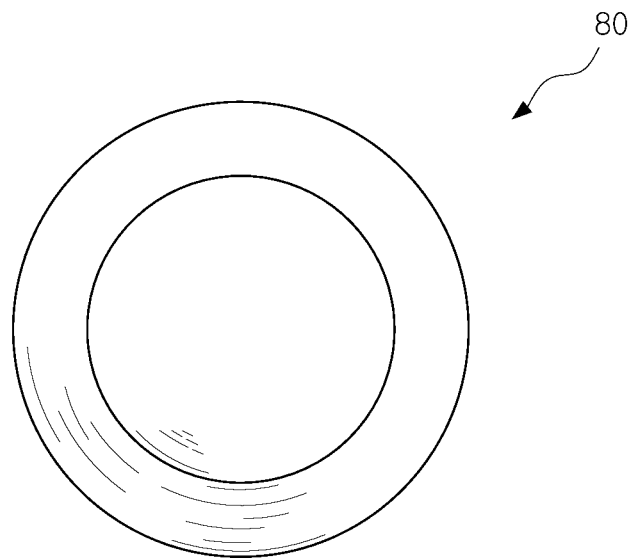
Figure 12A:
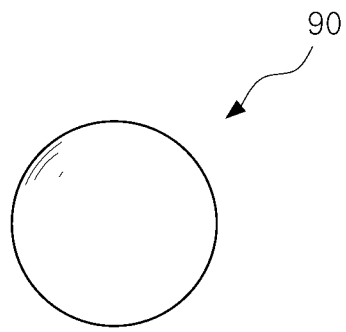
FIGS. 12a and 12b show a ball head according to one embodiment of the present invention.
Figure 12B:
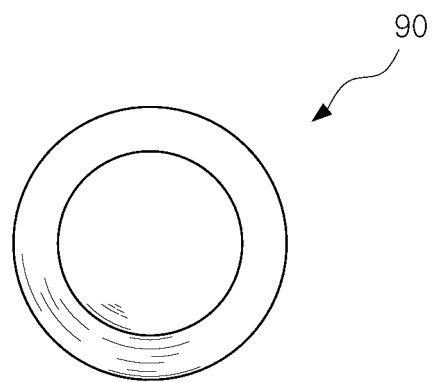

Moreover, the dual mobility acetabular cup assembly according to the present invention further comprises an insert 80 and a ball head 90. FIGS. 11a and 11b shows an insert and FIGS. 12a and 12b shows a ball head.

The insert 80 is placed at the inner-side face 44 of the liner 40, and the ball head 90 is disposed at an inner side of the insert 80. Inner-side face 44 of the liner 40 forms a liner cavity. The ball head 90 is mounted on the femoral stem (not shown). The outer face of the insert 80 corresponds to the shape of the inner-side face of the liner 40 and the outer face of the ball head 90 corresponds to the shape of the inner side of the insert 80. As shown in the drawings, the outer face of insert 80 has a semi-spherical configuration that is free of protrusions projecting therefrom. As such, insert 80 is freely rotatable within the liner cavity relative to the liner 40.

In the above, the applicant described various embodiments of the present invention. It should be interpreted that such embodiments are merely examples which implement the technical idea and any modification or revision falls within the scope of the present invention if it implements the technical idea of the present invention, however.

REFERENCE NUMERALS

1: dual mobility acetabular cup assembly
20: shell
22: space
24: outer face
26: inner face
30: penetration hole
34: hole
40: liner
42: outer-side face
44: inner-side face
46: protrusion
60: plug
62: external thread
64: through-hole
80: insert
90: ball head
400: dual mobility cup
410: acetabular cup
412: hole
420: liner
422: rim
430: insert
440: ball head

The invention claimed is:

1. A dual mobility acetabular cup assembly for an artificial hip joint comprising:
    a shell having a penetration hole and an inner side at least partially bounding a shell cavity;
        a liner disposed at least partially within the shell cavity directly against the inner side of the shell, the liner having an inner side at least partially bounding a liner cavity, a protrusion projecting from the liner and being received within the penetration hole;
        a plug disposed within the penetration hole, the plug having a through-hole configured to receive the protrusion; and
        an insert rotatably disposed at least partially within the liner cavity, the insert having an outer side that is disposed directly against the inner side of the liner;
        wherein the insert is freely rotatable within the liner cavity relative to the liner.

2. The dual mobility acetabular cup assembly of claim 1, wherein the protrusion is configured to fix the liner in the shell by being inserted in the penetration hole.

3. The dual mobility acetabular cup assembly of claim 1, wherein the penetration hole is tapered outwardly from an inner face of the shell.

4. The dual mobility acetabular cup assembly of claim 3, wherein the protrusion has a shape corresponding to the tapered penetration hole for fit connection to the penetration hole.

5. The dual mobility acetabular cup assembly of claim 1, wherein the protrusion and the through-hole are engaged by taper connection.

6. The dual mobility acetabular cup assembly of claim 1, wherein external threads are formed in an outer circumferential face of the plug and engage internal threads formed in the penetration hole.

7. The dual mobility acetabular cup assembly of claim 6, wherein the protrusion is tapered in an outward direction from a surface of the liner and the through-hole of the plug is tapered and receives the protrusion.

8. The dual mobility acetabular cup assembly of claim 1, wherein the shell is made from titanium.

9. The dual mobility acetabular cup assembly of claim 1, wherein the liner is made from one of cobalt-chrome or ceramic.

10. The dual mobility acetabular cup assembly of claim 1, wherein the protrusion is engaged with the shell by a taper connection.

11. The dual mobility acetabular cup assembly of claim 1, wherein the liner is free of any outwardly protruding rim.

12. The dual mobility acetabular cup assembly of claim 1, the insert having an inner side at least partially bounding an insert cavity.

13. The dual mobility acetabular cup assembly of claim 12, wherein the insert cavity is semi-spherical.

14. The dual mobility acetabular cup assembly of claim 12, wherein the insert is configured to be disposed between the liner and a femoral implant during use.

15. The dual mobility acetabular cup of claim 1, wherein the insert is free of protrusions projecting from the outer side thereof.

16. The dual mobility acetabular cup of claim 15, wherein the outer side of the insert has a semi-spherical configuration.

* * * * *